United States Patent [19]

Au

[11] 4,391,630

[45] Jul. 5, 1983

[54] CYANO-(4-CYANOPHENYL)METHYL ETHYL ESTER OF CARBONIC ACID USEFUL AS AN AGENT FOR SELECTIVE CONTROL OF BARNYARD GRASS

[75] Inventor: Andrew T. Au, Needham, Mass.

[73] Assignee: The Dow Chemical Company, Midland, Mich.

[21] Appl. No.: 354,480

[22] Filed: Mar. 3, 1982

[51] Int. Cl.$^3$ .................... A01N 47/06; C07C 121/75
[52] U.S. Cl. ........................................ 71/105; 260/463
[58] Field of Search ......................... 260/463; 71/105; 424/301

[56] References Cited

U.S. PATENT DOCUMENTS

| | | | |
|---|---|---|---|
| 3,124,608 | 3/1964 | Schisla et al. | 260/463 |
| 3,306,880 | 2/1967 | Lee et al. | 260/77.5 |
| 3,377,155 | 4/1968 | Weil et al. | 71/105 |
| 3,574,594 | 4/1971 | Gough et al. | 71/105 |
| 3,594,400 | 7/1971 | Boogaart et al. | 260/463 |
| 3,723,625 | 3/1973 | Boogaart et al. | 424/301 |
| 3,835,176 | 9/1974 | Matsuo et al. | 260/465 D |
| 4,247,475 | 1/1981 | Ching | 260/465 D |

FOREIGN PATENT DOCUMENTS 1122658  8/1965  United Kingdom .

OTHER PUBLICATIONS

Hibernia–Chemie G.m.b.H., Chemical Abstracts, vol. 65, 5374g (1966).

Uff et al., "Formation of Cyanohydrin Carbonates of Aromatic Aldehydes and Aryl Heteroaryl Ketones", *Synthetic Communications*, 8 (3), 163–167, (1978).

*Primary Examiner*—Donald G. Daus
*Assistant Examiner*—Diana G. Rivers
*Attorney, Agent, or Firm*—Norman L. Sims; Douglas N. Doline

[57] ABSTRACT

Disclosed as a novel compound is cyano-(4-cyanophenyl)methyl ethyl ester of carbonic acid. This compound has utility as an agent for selective control of barnyard grass.

3 Claims, No Drawings

CYANO-(4-CYANOPHENYL)METHYL ETHYL ESTER OF CARBONIC ACID USEFUL AS AN AGENT FOR SELECTIVE CONTROL OF BARNYARD GRASS

BACKGROUND OF THE INVENTION

Various alpha-cyano carbonates are taught in the literature. Cyanophenylmethyl ethyl ester of carbonic acid and the method of preparing such is taught by Uff et al. in "Formation of Cyanohydrin Carbonates of Aromatic Aldehydes and Aryl Heteroaryl Ketones", *Synthetic Communications,* 8 (3), 163–167 (1978).

SUMMARY OF THE INVENTION

The present invention is directed to the compound cyano-(4-cyanophenyl)methyl ethyl ester of carbonic acid. This compound has been found to be an active barnyard grass control agent. This compound is represented by the formula

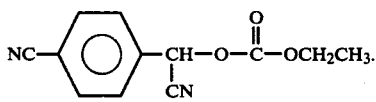

The compound of the invention is an oily liquid which is substantially insoluble in water, slightly soluble in nonpolar hydrocarbons and substantially soluble in polar organic solvents.

The cyano-(4-cyanophenyl)methyl ethyl ester of carbonic acid may be prepared by contacting a solution of 4-cyanobenzaldehyde and ethylchloroformate in a nonreactive water-immiscible organic solvent, such as methylene chloride, with an aqueous solution of a metal cyanide, preferably an alkali or alkaline earth metal cyanide, such as sodium cyanide, and if desired, a catalyst such as a phase transfer "onium" salt such as tetra-n-butylammonium chloride or benzyltrimethylammonium chloride, and stirring the mixture for about 1 hour to several days, preferably about 3 to 6 hours.

The product can then be recovered by washing, drying and concentrating the organic layer. Between about 0.1 and 40.0 equivalents of ethyl chloroformate for each equivalent of 4-cyanobenzaldehyde may be used, and between about 1.0 and 1.2 equivalents is preferred. Between about 1.0 and 20.0 equivalents of the metal cyanide per equivalent of the 4-cyanobenzaldehyde may be used, and between about 1.5 and 2.0 equivalents is preferred. The phase transfer catalyst is effective between about 0 and 10.0 equivalents per equivalent of 4-cyanobenzaldehyde, and between about 0.01 and 0.1 equivalent is preferred. The reaction may be run either with or without the catalyst. The reaction may be run between about $-30°$ C. and $60°$ C., and between about $-10°$ C. and $25°$ C. is preferred.

DESCRIPTION OF SOME PREFERRED EMBODIMENTS

The following example illustrates the present invention and the manner by which it can be produced, but, as such, should not be construed as a limitation upon the overall scope of the invention.

EXAMPLE 1

To a stirred solution of 2.0 g of sodium cyanide in 10 ml of water and a catalytic amount of tetra-n-butylammonium chloride at $0°$ C. is added dropwise 30 ml of methylene chloride containing 2.62 g of 4-cyanobenzaldehyde and 2.2 g of ethylchloroformate. The mixture is stirred overnight while being warmed to room temperature. The organic layer is washed with water followed by a saturated bicarbonate solution, then dried over magnesium sulfate and concentrated to 3.65 g of an oil giving a yield of 79.4 percent. Thin-layer chromatography, nuclear magnetic resonance spectroscopy and infrared spectroscopy all showed the product to be cyano-(4-cyanophenyl)methyl ethyl ester of carbonic acid.

The compound of the present invention can be employed for the selective control of barnyard grass in the presence of other plants, such as, for example, soybeans, white winter wheat and corn. For such use, the compound can be employed in an unmodified form or dispersed on a finely divided inert solid and employed as dust. Such mixture can also be dispersed in water with or without the aid of a surface active agent and the resulting aqueous suspension or dispersion employed as a spray. In other procedures, the compound can be employed as the active constituent in solvent solutions, oil-in-water or water-in-oil emulsions. The augmented compositions are adapted to be formulated as concentrates and subsequently diluted with additional liquid or solid adjuvants (such as inert horticultural carriers) to produce the ultimate treating compositions.

The exact concentration of the toxicant to be employed in the treating compositions is not critical and may vary considerably provided the required dosage of the effective agent is supplied. The concentration of toxicant in liquid compositions generally is from about 0.0001 to about 50 percent by weight. Concentrations up to about 95 percent by weight are oftentimes conveniently employed. In dusts, the concentrations of the toxicants can be from about 0.1 to 95 percent by weight. For use as a spray, it is often convenient to apply the compound as wettable powders.

In a representative operation, cyano-(4-cyanophenyl)methyl ethyl ester of carbonic acid, when applied as the sole toxicant in an aqueous dispersion at 4000 parts per million parts of the ultimate dispersion, was found to give 100 percent post-emergent kill of barnyard grass.

What is claimed is:

1. Cyano-(4-cyanophenyl)methyl ethyl ester of carbonic acid.

2. A method of selectively controlling barnyard grass which comprises subjecting barnyard grass to the compound of claim 1.

3. A herbicidal composition comprising an inert horticultural carrier and as a herbicide, the compound of claim 1, the concentration of said herbicide being from 0.0001 to about 50 percent by weight.

* * * * *